United States Patent
Star-Lack et al.

(10) Patent No.: US 8,199,873 B2
(45) Date of Patent: Jun. 12, 2012

(54) METHODS OF SCATTER CORRECTION OF X-RAY PROJECTION DATA 2

(75) Inventors: Josh Star-Lack, Palo Alto, CA (US); Mingshan Sun, Sunnyvale, CA (US)

(73) Assignee: Varian Medical Systems Inc., Palo Alto, CA (US)

( * ) Notice: Subject to any disclaimer, the term of this patent is extended or adjusted under 35 U.S.C. 154(b) by 239 days.

(21) Appl. No.: 12/760,851

(22) Filed: Apr. 15, 2010

(65) Prior Publication Data

US 2011/0255656 A1 Oct. 20, 2011

(51) Int. Cl.
*A61B 6/03* (2006.01)
(52) U.S. Cl. .......................................................... 378/7
(58) Field of Classification Search .................. 378/4, 7, 378/86–90; 382/131
See application file for complete search history.

(56) References Cited

U.S. PATENT DOCUMENTS

| | | | |
|---|---|---|---|
| 6,687,326 B1 * | 2/2004 | Bechwati et al. .................. | 378/7 |
| 2002/0048339 A1 * | 4/2002 | Schneider et al. ................. | 378/7 |
| 2008/0253515 A1 * | 10/2008 | Bertram et al. .................. | 378/62 |
| 2009/0290682 A1 | 11/2009 | Star-Lack | |

OTHER PUBLICATIONS

Schmidtlein et al., Validation of Gate Monte Carlo simulations of the GE Advance/Discovery LS PET scanners, 2006, Medical Physics, vol. 33, No. 1, pp. 198-208.*
Reitz, Development and evaluation of a method for scatter correction in kV Cone Beam Computer Tomography, Apr. 30, 2008, Doctoral Dissertation, Ruperto-Carola University of Heidelberg, Germany.*
Atherton et al., CT doses in cylindrical phantoms, 1995, Physics in Medicine and Biology, vol. 40, pp. 891-911.*
Jarry et al., A Monte Carlo-based method to estimate radiation dose from spiral CT: from phantom testing to patient-specific models, 2003, Physics in Medicine and Biology, pp. 2645-2663.*

* cited by examiner

*Primary Examiner* — Edward Glick
*Assistant Examiner* — John Corbett
(74) *Attorney, Agent, or Firm* — Deborah Wenocur; Jack Lin

(57) ABSTRACT

A system and method for forming an adjusted estimate of scattered radiation in a radiographic projection of a target object, which incorporates scattered radiation from objects adjacent to the target object, such as a patient table. A piercing point equalization method is disclosed, and a refinement of analytical kernel methods which utilizes hybrid kernels is also disclosed.

46 Claims, 16 Drawing Sheets

METHODS OF SCATTER CORRECTION OF X-RAY PROJECTION DATA 2

CROSS REFERENCE TO RELATED APPLICATIONS

This application is related to commonly owned U.S. patent application Ser. No. 12/125,053, filed on May 21, 2008.

FIELD OF THE INVENTION

This invention relates to the correction of the effects of scattered radiation on the x-ray radiographic projection of an object and in particular as applied to Computerized Tomography (CT).

BACKGROUND

Referring to FIGS. 1a and 1b, computerized tomography (CT) involves the imaging of the internal structure of an object 102 by collecting several projection images ("radiographic projections") in a single scan operation ("scan"), and is widely used in the medical field to view the internal structure of selected portions of the human body. Typically, several two-dimensional projections are made of the object at different projection angles, and a three-dimensional representation of the object is constructed from the projections using various tomographic reconstruction methods. From the three-dimensional image, conventional axial, coronal, or sagittal CT slices through the object can be generated. The two-dimensional projections are typically created by transmitting radiation from a "point source" 105 through the object 102, which will absorb some of the radiation based on its size, density, and atomic composition, and collecting the non-absorbed radiation onto a two-dimensional imaging device, or imager 110, which comprises an array of pixel detectors (simply called "pixels"). In the typical CT system, the radiation source 105 and imaging detector 110 are mounted on a gantry 150 which rotates them around the object 102 being scanned. Such a system is shown in FIG. 1a. A line that goes through the point radiation source 105, the center of rotation (known as the isocenter), and is perpendicular to the two-dimensional imager 110 is called the projection axis 112. The point where the projection axis hits the detector is known as the piercing point of the detector. Typically, the detector piercing point is located at or near the center of the imager in full-fan geometry (also known as centered-detector geometry). Described below is a variation called half-fan (offset-detector) geometry, wherein the detector array is offset, thus allowing for an increase in the field-of-view (FOV) with a 360 degree scan rotation.

The source's radiation emanates toward the imaging device 105 in a volume of space defined by a right-circular, elliptical, or rectangular cone having its vertex at the point source and its base at the imaging device. For this reason, the radiation is often called cone-beam (CB) radiation. Most commonly, the beam is collimated near the source into a rectangular cone or pyramid so that, when no object is present, the beam radiation only falls on the detector and not outside the detector boundaries. Generally, when no object is present within the cone, the distribution of radiation is substantially uniform on the imager. However, the distribution of the radiation may be slightly non-uniform. In any event, any non-uniformity in the distribution can be measured in a calibration step and accounted for. The projection axis may not be at the center of the imager or the center of the object. It may pass through them at arbitrary locations including very near the edge.

FIG. 1b shows further aspects of the CT system of FIG. 1a, including gantry 150 and controller 155. Controller 155 is coupled to radiation source 105, imaging device 110, and user interface 115. User interface 115 provides a human interface to controller 155 that enables the user to at least initiate a scan of the object, and to collect measured projection data from the imaging device. User interface 115 may be configured to present graphic representations of the measured data.

In an ideal imaging system, rays of radiation travel along respective straight-line transmission paths from the source, through the object (where they are partially absorbed), and then to respective pixel detectors without generating scattered rays that are detected. However, in real systems, when a quantum of radiation is absorbed by a portion of the object, one or more scattered rays are often generated that deviate from the transmission path of the incident radiation. These scattered rays are often received by "surrounding" detector elements that are not located on the transmission path that the initial quantum of radiation was transmitted on, thereby creating measurement errors.

The measurement errors created by scattered radiation cause artifacts and loss of spatial and contrast resolution in the radiographic projection data and the CT images produced by the radiation imaging system. The scattered radiation can also cause numerical errors in the image reconstruction algorithms (generally referred to as "CT number problems" in the art). All of the foregoing leads to image degradation.

Scattered radiation may arise from many sources. These may include: the bow-tie filter (if present), the object being scanned, an anti-scatter grid (if present), and the detector housing. One model for addressing these aforementioned scattering sources is described in U.S. patent application Ser. No. 12/125,053, filed on May 21, 2008, corresponding to patent publication number 20090290682, published Nov. 26, 2009. This application is hereby incorporated by reference in its entirety.

As indicated by both experiment and by Monte Carlo simulations, different types of objects can have different scattering properties and if they are all in the imaging field-of-view at the same time, then they must be appropriately addressed by a scatter correction method. For example, a significant amount of scatter can come from objects (e.g., supporting structures) adjacent to the actual object(s) of interest (e.g., the human body). One type of supporting structure is the patient table which is commonly made of polycarbon, a light material having a high probability of Compton interactions. It has been found that the scatter correction method described in the incorporated application may not be optimized to effectively model scatter from sources such as the patient table, due to how its shape, position, density, and material composition differ from that of the human body. As a result, scatter is underestimated for some projections, and a cupping artifact is observed in patients below the isocenter region when using the half-fan geometry with an offset detector (described and shown in FIG. 2). A method and system for estimating and correcting for scatter from multiple types of objects including the patient table is described hereinafter.

SUMMARY OF THE INVENTION

Disclosed herein are systems, methods, computer-program products, and computer-readable media for forming an estimate of total scattered radiation in a radiographic projection of a target object positioned adjacent to or on an adjacent structure or object such as a patient table. One such method includes:
a) generating at least one radiographic projection of the target object;
b) forming a first scatter correction estimate of the radiographic projection, the first scatter correction estimate not including scatter from an adjacent object that is at least partially adjacent to the target object;
c) separately forming a second scatter correction estimate of the radiographic projection, the second scatter correction estimate including scatter from the adjacent object; and
d) generating the total estimate of scattered radiation by summing the first scatter correction estimate and the second scatter correction estimate.

DETAILED DESCRIPTION

The inventive methods will be described according to embodiments addressing scattering from a scattering object adjacent to the target object or object of interest. An example thereof is a patient table which acts as a supporting structure for the object of interest. These embodiments are exemplary and not limiting. The methods and systems described herein can be applied to scattering from other objects adjacent to the object of interest.

The methods and associated systems and computer program products may be used alone or in various combinations with one another. As used herein and in the claims, the action of obtaining an item, such as an estimate of a quantity, encompasses the action of receiving the item from an outside process, computer-program product, and/or system, and the action of generating the item by the claimed process, computer-program product, or system.

The radiographic projections described herein are generated by a two-dimensional imaging device irradiated by a radiation source spaced therefrom to provide a space for the object of interest. The imaging device measures incident radiation at a plurality of pixels at corresponding locations on a two-dimensional surface, and the radiographic projection comprises a two-dimensional surface and a plurality of radiation values corresponding to a plurality of pixel locations of the imaging device. Each radiation value or amount includes a primary radiation amount representative of the radiation reaching the corresponding pixel along a direct path from the radiation source and a scattered radiation amount representative of other radiation reaching the corresponding pixel.

Exemplary method embodiments broadly comprise obtaining an estimate of a radiation amount associated with a first location of the radiographic projection, the radiation amount comprising at least one of a radiation amount emitted by the radiation source, a scattered radiation amount, or the primary radiation amount at the first location. The exemplary methods further comprise storing the estimate of the scattered radiation in a computer-readable medium.

Exemplary computer-program product embodiments broadly comprise instruction sets embodied on a computer-readable medium which, when executed by a processor of a computer system, cause the processor to implement the actions of the exemplary method embodiment. Exemplary system embodiments broadly encompass a radiation source, a two-dimensional imaging device, a processor, and a set of instructions stored on a computer-readable medium to implement actions that include the actions of the above exemplary method embodiment.

Figure 2:
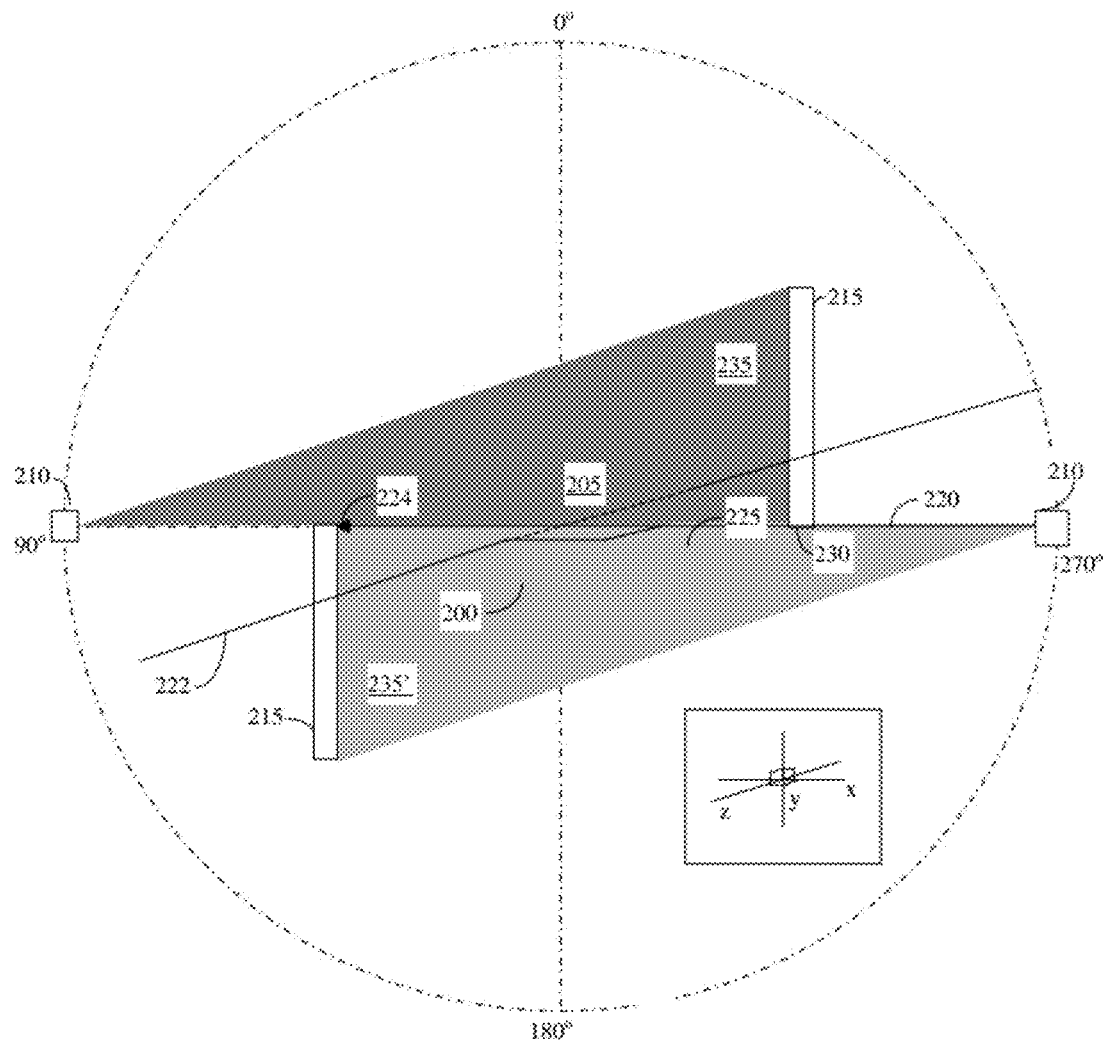
FIG. 2 is a transaxial view showing an exemplary configuration of the patient table with respect to the object on the table (generally the patient), the radiation source, and the detector, for two different (opposing) radiation angles as provided by rotation of the gantry about the object. The half-fan (or offset-detector) geometry is illustrated. Two projections, situated 180 degrees apart, are shown.

FIG. 2 shows an exemplary configuration of a patient table 200 with respect to the object 205 on the table (generally the patient), the radiation source 210, and the detector 215, for two different radiation angles as provided by rotation of the gantry about the object along a circular trajectory 212. In this example, system coordinates are defined with respect to the isocenter and the table angle. In FIG. 2, the xy plane is defined as the plane of the paper. The z axis extends out from the paper. The axes are shown in the insert: line 220 corresponds to the x-axis, line 222 corresponds to the z-axis. The angle is defined as 0 degrees when piercing point ray 220 (defined herein as a ray from x-ray source 210 perpendicularly through the isocenter line 222, hitting the detector 215 at piercing point 224) is directed perpendicularly to table surface 225, and is defined as 90 degrees or 270 degrees when incident radiation beam is directed parallel to table surface 225. Herein the direction of increasing angle will be defined as counter clockwise: i.e., 90 degrees is defined as being the leftmost source point. Detector 215 is disposed substantially opposite radiation source 210. However, in the half-fan geometry shown herein, the detector is offset from the projection axis so that one edge 230 is substantially opposite radiation source 210. The half-fan geometry illustrated herein is defined as being offset to the left. To completely define the system coordinates, the direction of detector offset must be specified. Triangles 235 and 235' ("half-fans") represent the fields-of-view of the projections at 90 and 270 degrees respectively.

Figure 3:
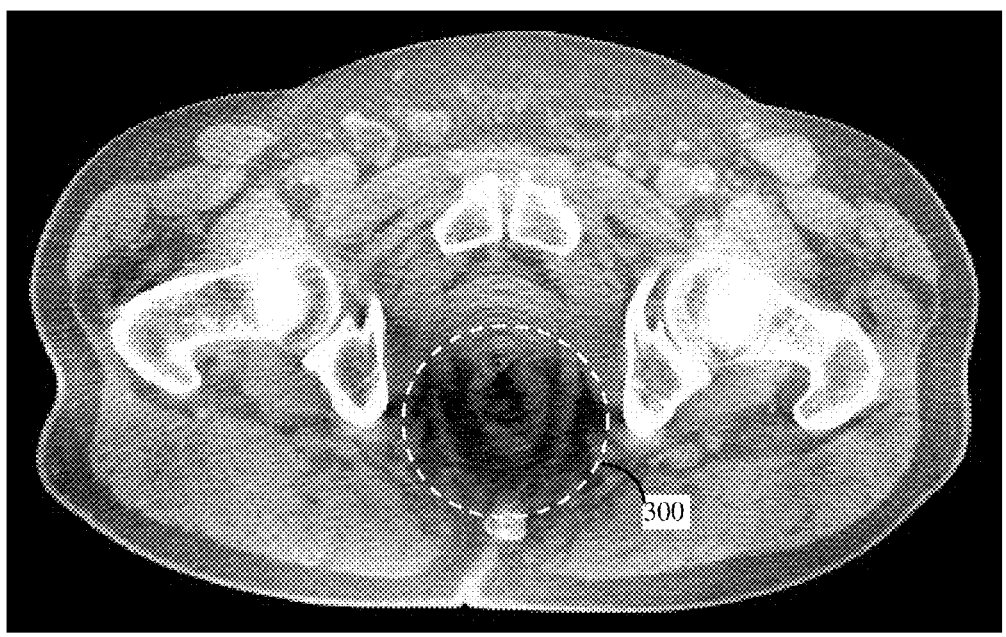
FIG. 3 shows an example of a CT projection with a cupping artifact 300 caused by scatter from the patient table.

FIG. 3 shows an example of a CT pelvis slice with cupping artifact 300 caused by scatter from the patient table. The patient table scatter artifact is most severe in situations with high scatter-to-primary ratios (SPR's) such as pelvis scans.

Figure 4:
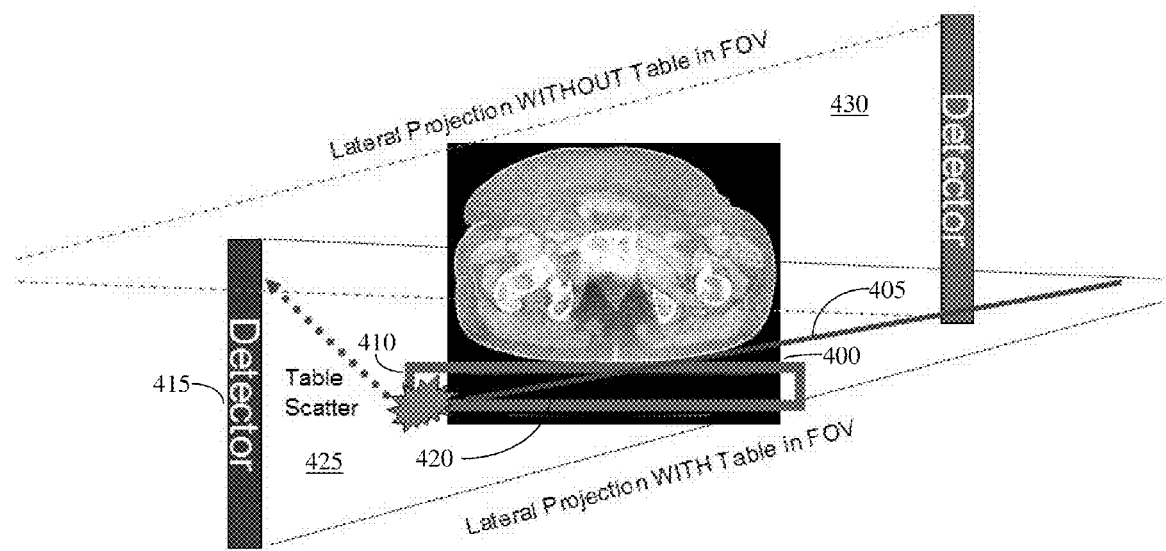
FIG. 4 is a diagram showing how the influence of patient table scatter is magnified for lateral views.

As shown in FIG. 4, the influence of patient table scatter is magnified for lateral views, i.e., where the radiation angle as defined above is near 90 degrees or 270 degrees. In that case, table top surface 400 is parallel or nearly parallel to x-ray beam 405, and table exit surface 410 (which is a scattering medium) is situated relatively close to detector 415, thus yielding an unobstructed path for scattered radiation to hit the detector. For the half-fan detection geometry shown, the table 420 is in the field-of-view only for projection 425 (270 degrees as defined), but not for projection 430 (90 degrees as defined).

Herein two exemplary methods are disclosed which may be applied to forming an estimate of total scattered radiation in a radiographic projection of a target object positioned near an adjacent object, for example the target object positioned on a patient table, which include a separate correction for scattering from the adjacent object. These methods can be used to estimate scattering from the sources adjacent to the target object. The first exemplary method is an empirical method that exploits the data inconsistencies between opposing projections to determine a correction factor, where the scattering is largest on opposing lateral projections (this may be known hereinafter as "Piercing Point Equalization method"). The second exemplary method is an analytically based method that uses a hybrid kernel model for the point scatter profiles (this may be known hereinafter as "Hybrid Kernel Correction method"). Also disclosed are exemplary system embodiments related to the above mentioned exemplary methods which broadly encompass: a radiation source, a two-dimensional imaging device, a processor, and a set of instructions stored on a computer-readable medium to implement actions that include the actions of the above mentioned exemplary methods.

Piercing Point Equalization

The Piercing Point Equalization method described hereinafter is applicable to estimating scattering due to sources such as the patient table. It is further applicable in general to providing a correction to other scatter estimation methods.

A piercing point on the detector of a CT system is defined as the point where a primary ray, i.e. an unscattered ray, extending from the radiation source perpendicularly through the isocenter line (the axis of rotation about which the mechanical gantry rotates, or the z-axis as defined in FIG. 2) of the CT system intersects the detector. A piercing point ray, therefore, is a primary ray which extends from the source perpendicularly through the isocenter line to the detector.

The exemplary piercing point equalization method described hereinafter is based on the assumption that, in CT acquisitions, two piercing point rays taken 180 degrees apart should produce identical measurements. However, due to scatter from adjacent objects such as patient table scatter, two opposing piercing point measurements may not match. In this method as applied to patient table scatter, an initial scatter correction is made which takes into account many scattering sources. The assumption is made that, since other scattering sources have been addressed in the initial scatter correction, the difference between the higher and lower of the two opposing piercing point measurements (i.e., the amount of radiation received by the detector) may be due to table-induced scatter error. This error is calculated and a correction is then applied to the entire set of projections affected by scatter from the general adjacent object, e.g., a patient table. The correction is based on the difference between the two opposing, or nearly opposing, piercing point primary estimates after the initial scatter correction is made (for example, according to the kernel methods disclosed in incorporated application Ser. No. 12/125,053. These will be hereinafter termed the "standard kernel-based correction".)

Figure 5A:
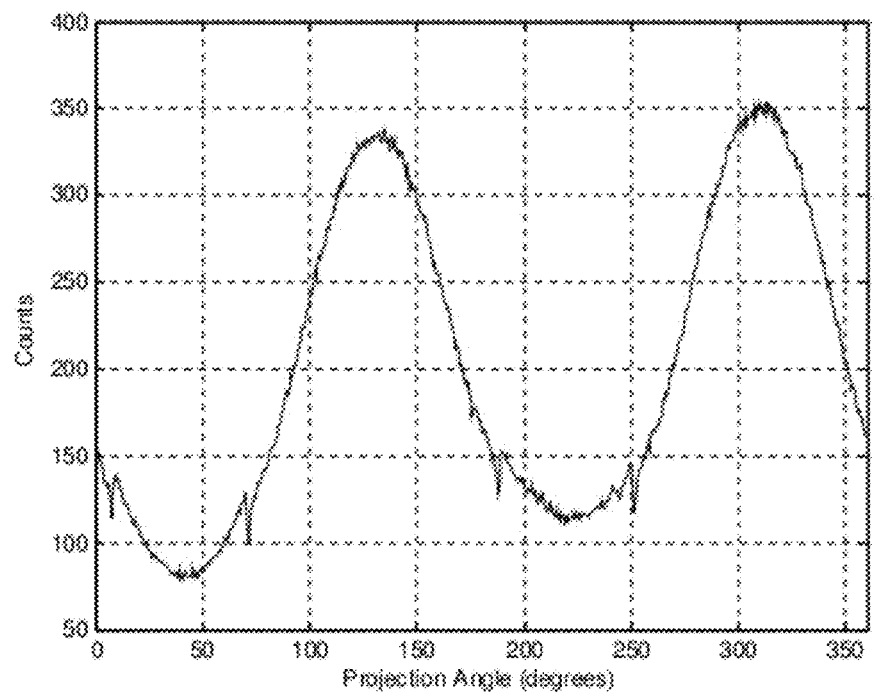
FIG. 5a shows an exemplary graph of piercing point projection values as a function of projection angle, before correction with the piercing point equalization correction.
Figure 5B:
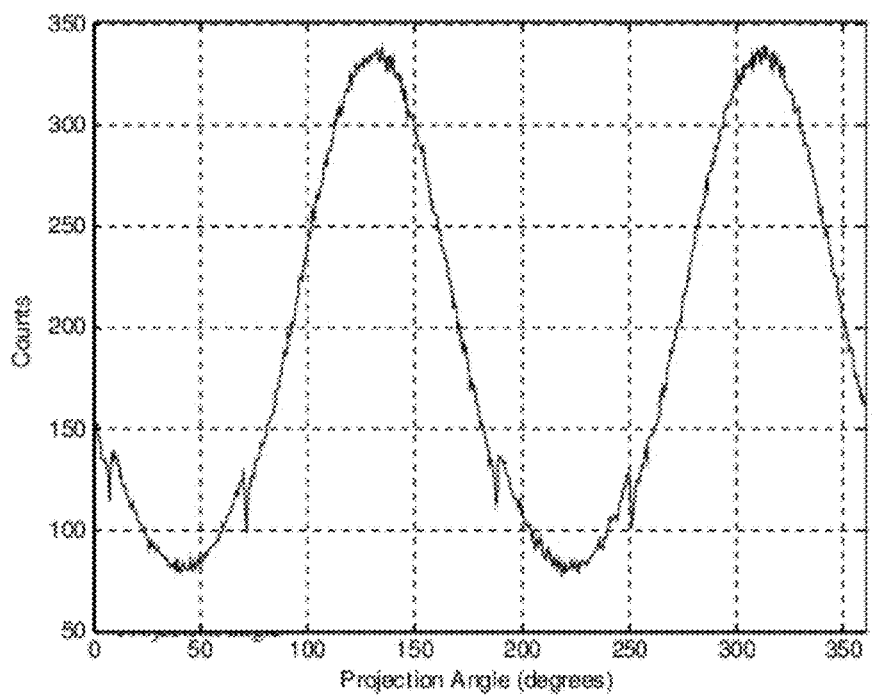
FIG. 5b shows an exemplary graph of piercing point projection values as a function of projection angle, after correction with the piercing point equalization correction.

FIGS. 5a and 5b show exemplary graphs of piercing point projection values as a function of projection angle, before (FIG. 5a) and after (FIG. 5b) correction with the piercing point equalization correction described below.

Figure 5C:
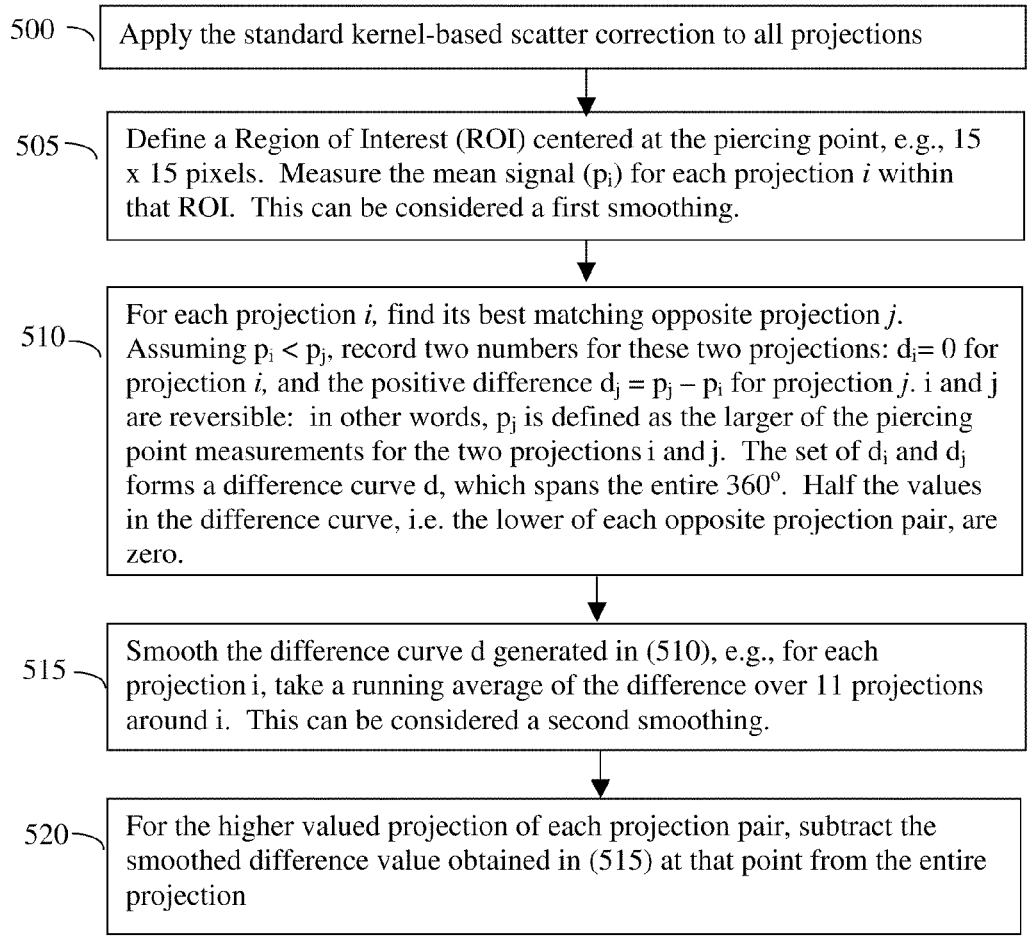
FIG. 5c shows a high level flow diagram of an exemplary piercing point method.

An embodiment of the piercing point equalization method is a delayed mode (or implementation). This is defined herein that extra processing is required after data acquisition finishes so that the viewing of the final images is delayed. This embodiment is illustrated hereinafter as applied to patient table scatter. This embodiment is straightforward to implement once a complete set of paired projections is available. Since scatter from the adjacent object, e.g., the table, is expected to vary from projection to projection, temporal smoothing (i.e., smoothing from one projection to the next) can be applied to the table scatter estimate to reduce noise-induced fluctuations. Assuming all projections are available, an exemplary algorithm of this method embodiment is described below and illustrated in FIG. 5c.

(500) Apply the standard kernel-based scatter correction to all projections.

(505) Define a Region of Interest (ROI) centered at the piercing point, e.g., 15×15 pixels. Measure the mean signal ($p_i$) for each projection i within that ROI. This can be considered a first smoothing.

(510) For each projection i, find its best matching opposite projection j. Assuming $p_i < p_j$, record two numbers for these two projections: $d_i = 0$ for projection i, and the positive difference $d_j = p_j - p_i$ for projection j. i and j are reversible: in other words, $p_j$ is defined as the larger of the piercing point measurements for the two projections i and j. The set of $d_i$ and $d_j$ forms a difference curve d, which spans the entire 360°. Half the values in the difference curve, i.e. the lower of each opposite projection pair, are zero.

(515) Smooth the difference curve d generated in step c), e.g., for each projection i, take a running average of the difference over 11 projections around i. This can be considered a second smoothing.

(520) For the higher valued projection of each projection pair, subtract the smoothed difference value obtained in step d) at that point from the entire projection.

Another embodiment of the piercing point equalization method is a real-time/quasi-real-time implementation (or mode). Real-time is defined herein that the reconstruction process can keep up with the data acquisition rate so that, as soon as the acquisition is finished, i.e., the gantry rotation completes, the final images are available. This embodiment is illustrated hereinafter as applied to patient table scatter, but can be applied to scatter from general adjacent objects. As is the case with the earlier described delayed implementation, the piercing point correction is applied after an initial scatter correction is made, which takes into account scattering from all sources but may not be optimized for sources such as the patient table.

To apply the piercing point correction in real time, the data is taken in such a way that the first 180 degrees of projections do not contain, or only contain minimal amounts of, table scatter. The correction does not need to be actually applied before the paired projections become available. This requires, in the best case, that the gantry starts at a certain angle and rotates in a certain direction, depending on the way the detector is offset which will be described in more detail below. In clinical settings, this requirement may not be met, which necessitates delaying until paired projections are available. The real-time/quasi-real-time embodiment provides a method for implementing the necessary delaying.

A practical way to delay the carrying out of the piercing point correction while data are being acquired and reconstructed is to cache projections. A projection is called "higher scatter" if it contains substantial adjacent object (e.g., table) scatter. In certain cases, depending on how the detector is offset, the rotation direction and start angle of rotation, no opposing lower scatter projection is yet available to match the piercing point intensity. In these cases, it is necessary to wait until the opposing projection becomes available at a later point in time. During the intervening time, the unpaired "higher scatter" projections are cached either in RAM memory, or on disk. Determination of the regions of expected higher and lower scatter projections, and the resulting requirements for caching, depends on several criteria. An exemplary, though not necessarily complete, set of the criteria used to determine caching, as illustrated with table scatter is:

1. Rays which go through the table but do not pass through the object evidence the relatively highest amount of table scatter. If such rays pass longitudinally through the table, i.e., have the longest relative traversal through the table, the table scatter is maximized. The highest scatter angle, according to this criterion, is 270 degrees as defined in FIG. 2, i.e., parallel to the table surface with the source to the right. This angle is the highest scatter for a half-fan geometry with the detector offset to the left, since, as shown in FIG. 4, the majority of rays pass longitudinally through the table and exit the table near to the detector. The lowest scatter angle is correspondingly 90 degrees, since as shown in FIG. 4, for the half fan geometry with detector offset to the left, the rays do not pass through the table at all for 90 degrees. In an embodiment, the 180 degrees of the circle with the lowest scatter angle in its center is defined as the lower scatter semicircle, whereas the 180 degrees of the circle with the highest scatter angle at its center is defined as the higher scatter semicircle. In the geometry of FIG. 4, the lower scatter semicircle is 0-180 degrees, the higher scatter semicircle is 180-360 degrees. This is further illustrated in FIG. 5d.
2. If rays which go through the table emerge close to the detector, the table scatter component is further increased.
3. If rays go through a long path through the object before reaching the table, there won't be as many scattered rays reaching the table, therefore the table scatter will be somewhat lowered. However, this scatter lowering effect is not as large as the scatter increasing effect of a ray emerging from the table near the detector.

Figure 5D:
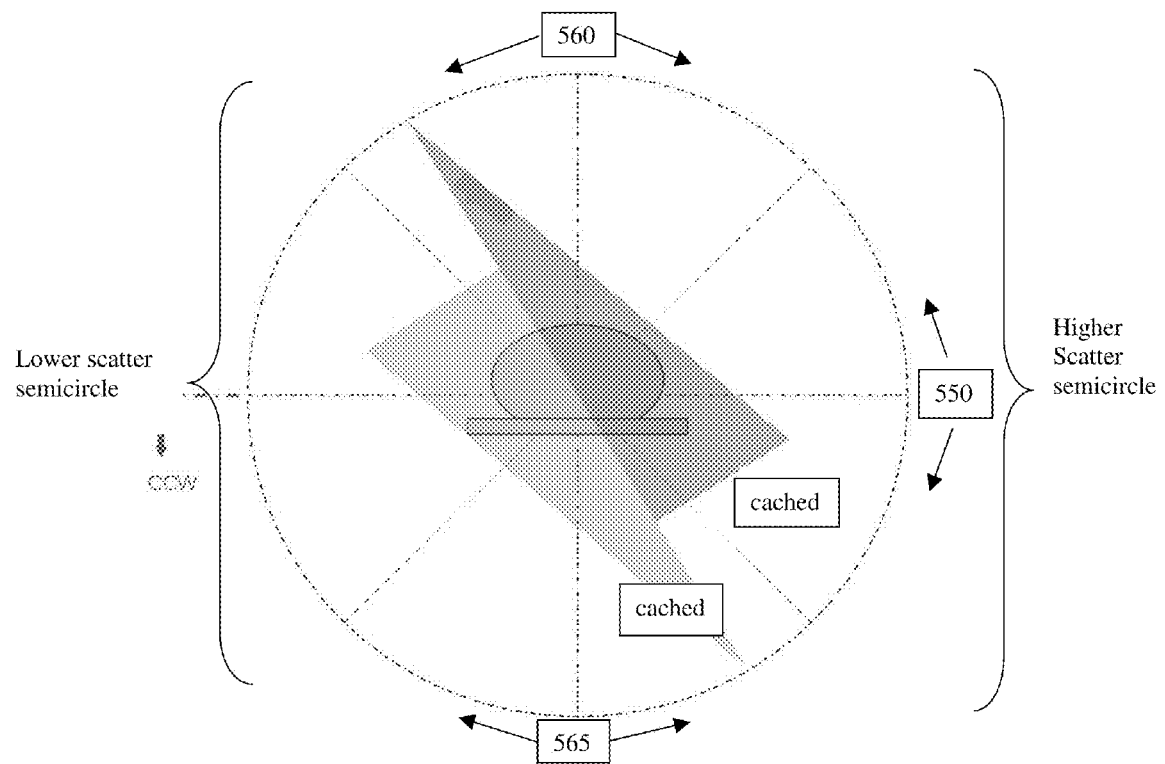
FIG. 5d shows examples of caching.

The amount of caching required depends, not only on the criteria listed above, but also on the initial position of the source and detector, the direction of rotation of the gantry, and the direction of offset of the detector. Some examples are illustrated in FIG. 5d.

1. For a gantry rotation 550 starting with the source at 270 degrees, the amount of projections required to be cached is about ¼ of the total projections, or 90 degrees worth of projections, whether the rotation is CW or CCW, since the first 90 degrees of projections are considered "high scatter", and there is no opposing projection available. The regions marked "cached" in the figure apply for initial source position of 270 degrees, with CW rotation.
2. For a gantry rotation 560 starting with the source at zero degrees, i.e., at the top, the amount of caching depends on the direction of rotation. For CCW rotation, no caching is necessary, since the first 180 degrees of projections are considered "low scatter", and when the "high scatter" projections are reached, opposing projections are available. On the other extreme, if the source starts at zero degrees and the rotation is CW, a full 180 of projections are "high scatter" without opposing projections available, and would ideally be cached. A similar situation exists for 180 degree initial position 565, although the directions are reversed.

Caching the projections may delay the time that the final image is reconstructed.

The time delay can be reduced by reducing the amount of projections that are cached. It is found in experimental studies that satisfactory results can still be achieved by caching less than the optimal range of projections, e.g., less than 90 degrees of projections for initial position of 90 or 270 degrees. 45 degrees of caching for 90 or 270 degree initial position has been found to give acceptable results in some cases.

Note that it is possible to cache an arbitrary number of projections, not just 45 or 90 degrees. Note also that the piercing point equalization, whether delayed or real-time, should be applied after kernel scatter correction but before the logarithm operation (described in incorporated application Ser. No. 12/125,053). Although mainly directed to table or other adjacent object scatter, the piercing point equalization method also tends to correct, or can be influenced by, any other inconsistencies such as detector gain and lag effects.

The piercing point equalization algorithm is easily implemented and is substantially blind to the particulars of the adjacent object scattering properties. Only a constant-value scatter estimate is determined for each projection. Another scattering model is an analytical model such as that described hereinafter.

Analytical Hybrid Kernel Model

The method described hereinafter is related to the kernel model described in incorporated patent application Ser. No. 12/125,053. Application Ser. No. 12/125,053 introduced asymmetric kernels to characterize scatter profiles. Asymmetric kernel modeling of the scattering profiles extended the results for estimated object scatter as compared to earlier symmetric kernel models. The symmetric and asymmetric kernel models are described in application Ser. No. 12/125, 053. The symmetric kernel model is termed Convolution Mode 0, and the asymmetric kernel model is termed Convolution Mode 1. The current method modifies the existing kernels where there is a shadow from a scattering source adjacent to the object, e.g., table shadow, in each projection, to reflect the additional scatter generated by the scattering source. These modified kernels are a blend of symmetric kernels and asymmetric kernels, and are termed "hybrid kernels". This method is illustrated hereinafter by an embodiment as applied to patient table scatter. The application to patient table scatter is not limiting: the method may be applicable to other scattering sources adjacent to the object.

For the exemplary patient table scatter embodiment, it has been found experimentally and by modeling such as Monte Carlo simulations that x-ray beams which pass mainly through the patient table and not through the target object are better modeled by a symmetric kernel, whereas beams that pass through the object are better modeled by an asymmetric kernel. This is possibly due to the differences in density, shape, and material composition between the table and the target object. For the beams passing through the patient table and the target object, a combination of symmetric and asymmetric kernels can be used. Referring back to FIG. 2, 0 degree beams have a larger asymmetric kernel contribution since most scatter is from the object, whereas 90 degree beams, i.e., lateral views, have a larger symmetric kernel contribution, since a higher proportion of scatter is from the table.

Accordingly, an embodiment of an algorithm is proposed that contains a spatially dependent mix of both symmetric and asymmetric kernels, with the mixing fraction depending on the table structure and the projection angle as follows:

HybridKernel=w·Kernel$_A$+(1−w)·Kernel$_B$ where Kernel$_A$ is the symmetric kernel, Kernel$_B$ is the asymmetric kernel, and w is a weighting factor, in an embodiment w being a function that depends on the geometry of the adjacent object, e.g., the table, and the gantry angle, and is calibrated with the aid of a slit scan as will be described.

As described in incorporated application Ser. No. 12/125,053, the incident radiation I$_I$ can be modeled as an array of pencil beams. In an embodiment of the hybrid kernel model, the hybrid kernels are only applied to pencil beams that pass through the adjacent object, e.g., the table. Thus, the algorithm requires knowledge of the projected adjacent object, e.g., table, shape and its position for each view. With this knowledge, the hybrid kernel modification can be implemented substantially within the existing algorithm framework.

Figure 6:
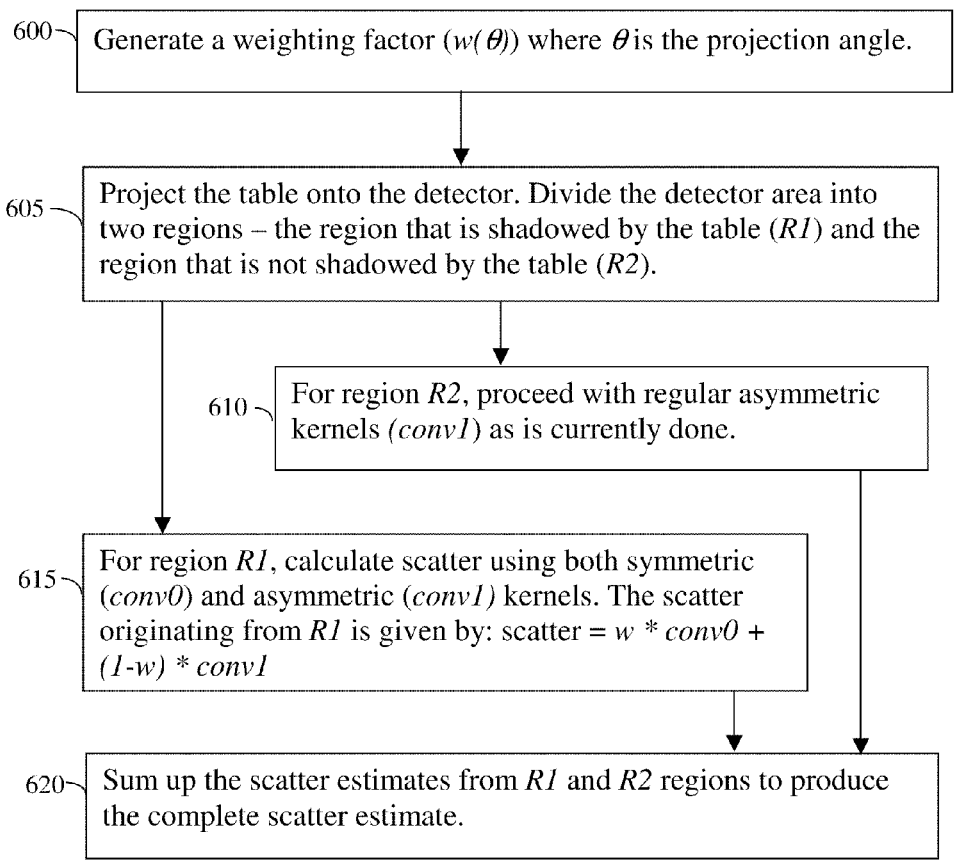
FIG. 6 shows a high level flow diagram of an exemplary hybrid kernel method.

FIG. 6 shows a high level flow diagram of an exemplary hybrid kernel method embodiment as applied to a patient table adjacent object.

For each projection,
1) Generate a weighting factor (w(θ)) where θ is the projection angle. (600)
2) Project the table onto the detector. Divide the detector area into two regions—the region that is shadowed by the table (R1) and the region that is not shadowed by the table (R2). (605) Segmentation and/or variable mask may be utilized.
3) Within the convolution loop:
   a. For region R2, proceed with regular asymmetric kernels (conv1). (610)
   b. For region R1, calculate scatter using both symmetric (conv0) and asymmetric (conv1) kernels. The scatter originating from R1 is given by: scatter=w*conv0+(1−w)*conv1 (615)
   c. Sum up the scatter estimates from R1 and R2 regions to produce the complete scatter estimate. (620)

Note that 3a and 3b can be rearranged during implementation such that the conv1 is performed all together for regions R1 and R2.

Following is a more detailed description of some of the above method steps. Determination of weighting function w (refer to step 600)

For each projection and each detector pixel shadowed by the table, the weighting function w defines how much of the total scatter signal is coming from the table (in some embodiments, "super-pixels" comprising multiple pixels are utilized in order to lower computation time). The weighting function specifies the fractional amplitude of the symmetric kernel relative to the total kernel amplitude. When the weight is 1, the kernel becomes completely symmetric; when it is 0, the kernel is asymmetric. The weighting function is projection-dependent and has a peak near the projection where the x-ray beam passes horizontally through the table (FIG. 2, 270° projection). In an embodiment, the weighting function is approximated as a symmetric Gaussian function $$w(\theta) = A_t e^{-\frac{(\theta-\theta_0)^2}{2\sigma^2}}, \qquad (2)$$

where θ is the projection angle and $A_t$, $\theta_0$ and σ are parameters to be determined. The function is evaluated in the range [$\theta_0$−180°, $\theta_0$+180°] to ensure its continuity upon the wrap-around at 360°. The weighting function depends on the type of table used, but for a given table, it has been found to be relatively independent of the scanned object shape and size.

Figure 7:
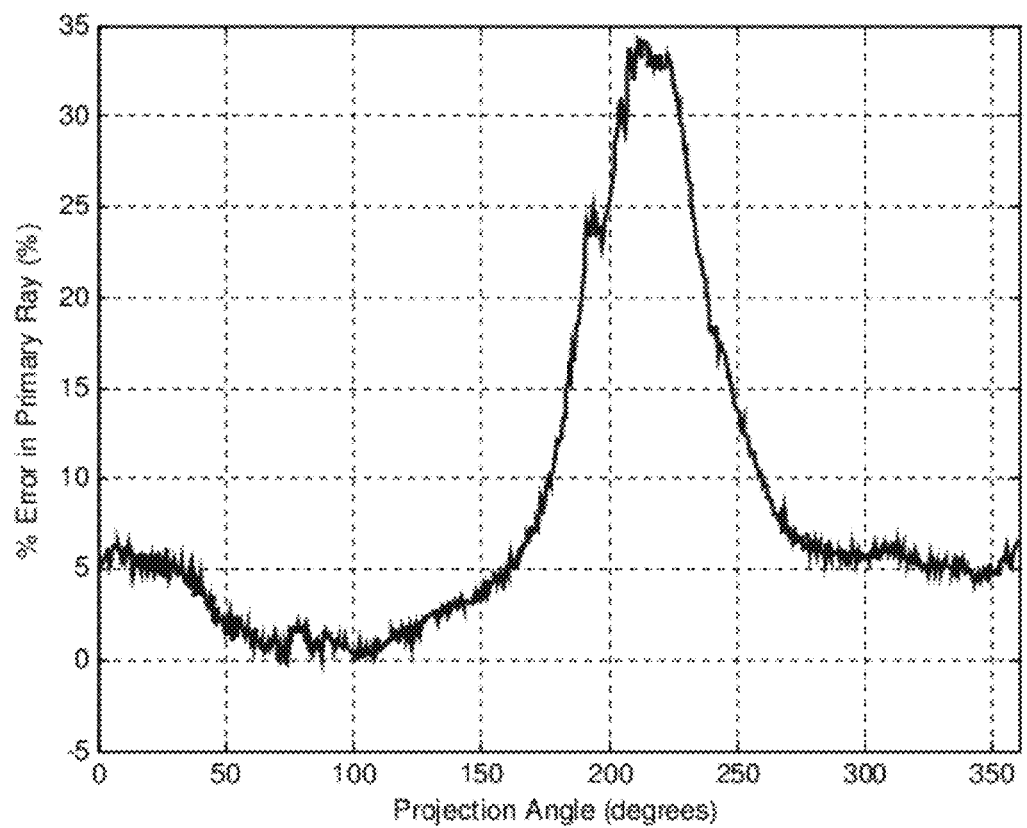
FIG. 7 is a particular instance of a graph of primary error vs projection angle near the piercing point, using the kernel algorithm with w=0.

In an embodiment, a set of experimental measurements known as slit-scan scatter measurements may be used to obtain the weighting function, i.e., to experimentally determine the weighting function for a particular patient table. The general technique used in this embodiment is to compare the existing kernel function correction with a slit-based correction which is considered to be the "gold standard" correction. Slit-based correction is described in U.S. Pat. No. 7,336,760, issued Feb. 26, 2008, which is hereby incorporated by reference in its entirety. Then, from the difference curve between the two corrections, fitting parameters may be determined for the functional form chosen for the weighting function. An exemplary weighting function determination is as follows:

A uniform elliptical phantom may be placed on the table and scanned with both wide and narrow slit beams. The wide scan may be corrected with the current kernel-based scatter correction algorithm. This is equivalent to a weighting function w=0 for all projections. The wide scan may also be corrected with the slit-based correction (scatter estimate=1.1*(wide−narrow)), which is considered to be the most accurate correction. From the slit-scan measurement, errors in the primary and scatter estimates using the standard kernel model may be determined and, from these results, a weighting function w may be generated. FIG. 7 is a particular instance of a graph of primary error versus projection angle near the piercing point, using the kernel algorithm with w=0. The error is considered to be caused by table scatter.

It is observed that the fitting parameters for the weighting function w(θ) are correlated with like parameters from the error curve of FIG. 7. For the Gaussian weighting function form of equation (2), two of the fitting parameters, $\theta_0$ (this parameter depends on where the 0° projection is, ranges from 0 to 360) and σ, (this parameter ranges from 15 to 40 degrees, with a typical value of 25 degrees) may be measured directly or indirectly from the peak location 705 and the FWHM 710 of the peak of the error curve. The third parameter in the weighting function, $A_t$ (which ranges between 0 and 1) may then be manually adjusted to minimize primary errors. In an example, the following values were found, $\theta_0$=210°, σ=25.5°, $A_t$=0.8.

Depending on the patient table geometry, a Gaussian form for the weighting function may not be optimal. Another possible form for the weighting function is a Gamma distribution.

Segmentation (Refer to Step 605)

In an embodiment of the hybrid kernel model as applied to table scatter, the hybrid kernels are applied to the pencil beams located only within parts of the projection that are shadowed by the adjacent object, e.g., the table. Thus it is important to be able to efficiently segment the adjacent object. The segmentation process will be illustrated with a patient table, although this is exemplary and not limiting.

Figure 8:
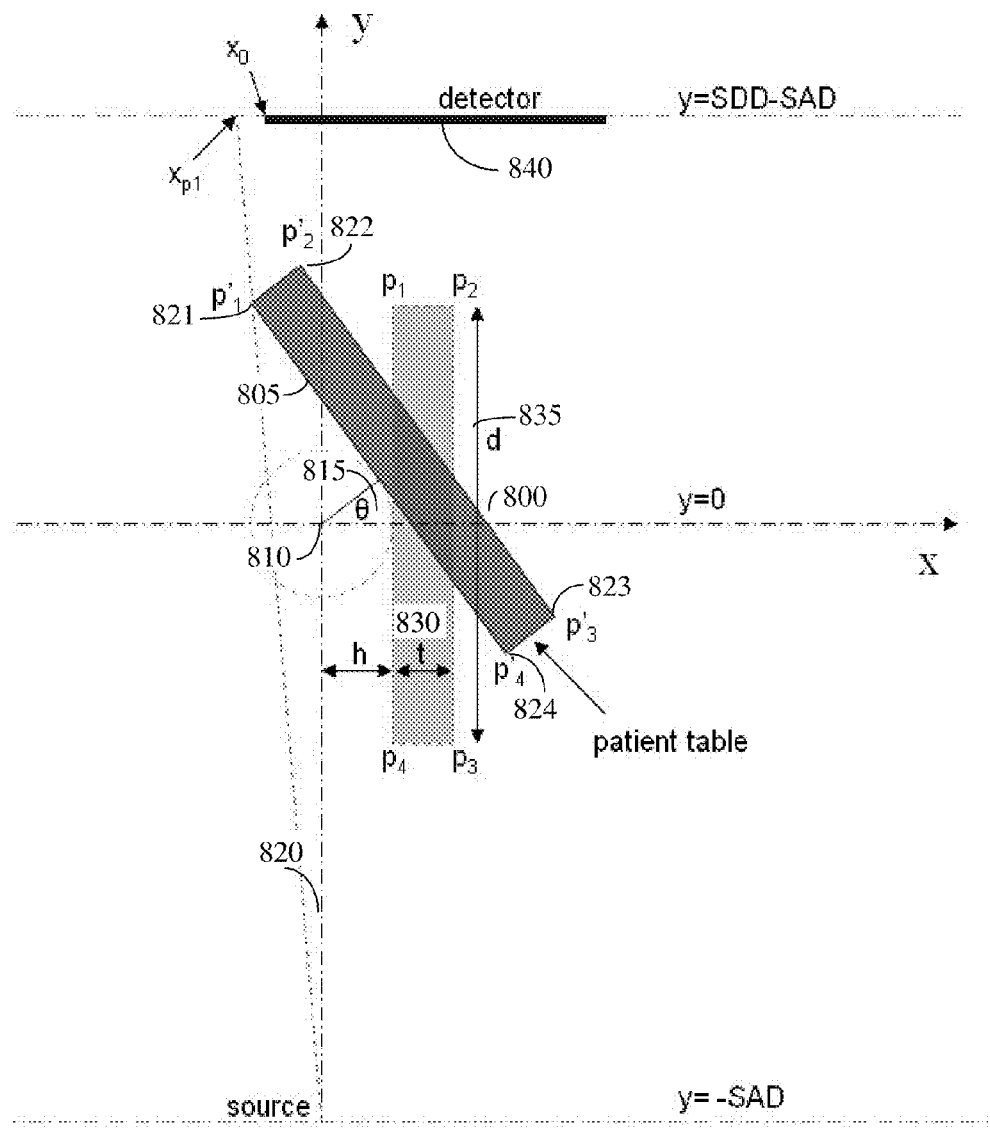
FIG. 8 shows a transaxial view of the source-detector system with the patient table in the field-of-view.

Although it may be possible to use image processing techniques to determine where the table shadow falls on the detector, it has been found to be more straightforward and more accurate to use a priori knowledge of the table shape and position to mathematically project the table onto the detector surface. An exemplary implementation of such a projection is as follows:

The four edges of the table are projected on the detector. For scans in which the table is uniform in its axial direction, this turns into projecting four parallel lines, or effectively four points due to the translational symmetry in the axial direction. FIG. 8 shows a transaxial view of the source-detector system with the patient table 800 in the field-of-view. Assuming the distance from the top 805 of the table to the isocenter 810 is h, and the angle 815 between the table 800 and the central ray 820 is θ, then the four corner points 821-824 of the table's cross section can be fully specified in the coordinate system defined as in FIG. 8. At θ=0, the four points are:

$$\begin{cases} p_1 : (x_1, y_2) = (h, d/2) \\ p_2 : (x_2, y_2) = (h+t, d/2) \\ p_3 : (x_2, y_1) = (h+t, -d/2) \\ p_4 : (x_1, y_1) = (h, -d/2), \end{cases} \quad (3)$$

where t is the table thickness 830, and d is the table's lateral width 835. At an arbitrary projection angle θ, the new coordinates of these four points are calculated by a rotational operation:

$$\begin{cases} x' = x\cos(\theta) - y\sin(\theta) \\ y' = x\sin(\theta) + y\cos(\theta). \end{cases} \quad (4)$$

Applying Eq. (4), the new coordinates are:

$$\begin{cases} p'_1 : (h\cos(\theta) - d/2\sin(\theta), h\sin(\theta) + d/2\cos(\theta)) \\ p'_2 : ((h+t)\cos(\theta) - d/2\sin(\theta), (h+t)\sin(\theta) + d/2\cos(\theta)) \\ p'_3 : ((h+t)\cos(\theta) + d/2\sin(\theta), (h+t)\sin(\theta) - d/2\cos(\theta)) \\ p'_4 : (h\cos(\theta) + d/2\sin(\theta), h\sin(\theta) - d/2\cos(\theta)). \end{cases} \quad (5)$$

New points $p'_1$, $p'_2$, $p'_3$ and $p'_4$ can then be projected onto the detector plane (defined to be in the x-plane) according to the following equation:

$$x_p = x \cdot \frac{SDD}{SAD + y}, \quad (6)$$

where SDD is the Source-to-Detector Distance and SAD is the Source-to-Isocenter (Axis) Distance. The units of Eq. (6) can be expressed in terms of the detector pixel index (or detector column index) as $$X_p = \frac{(x_p - x_0)}{\text{pixelsize}}, \quad (7)$$

where $x_0$ is the x coordinate of the first detector column. Note that the pixel index Xp may or may not be located within the actual detector matrix, so an intersection operation may be required.

After the four points are rotated and projected to the detector 840, the table shadow on the detector plane is defined. It is the area between two vertical lines passing through the leftmost and the rightmost points, with its width equal to the maximum separation among these four projected points. The part of the shadow that is actually seen by the detector is the intersection of the projected shadow and the detector area, that is, the starting and the ending column of the table shade are given by:

$$\begin{cases} X_1 = \max(\min(X_{p1}, X_{p2}, X_{p3}, X_{p4}), 1) \\ X_2 = \min(\max(X_{p1}, X_{p2}, X_{p3}, X_{p4}), NSizeX), \end{cases} \quad (8)$$

when the shadow does intersect with the detector. In this implementation, the table shadow or table mask is a binary 2-D map having values 1 and 0 for unshaded and shaded regions respectively.

Actual patient tables may not have exact rectangular cross sections. One possible alternate cross section is a trapezoidal cross section, which may be treated with the aforementioned scheme by adapting the coordinates for the table edges in Eq. 3. Alternately, a slightly non-rectangular cross section table may be approximated with a rectangular cross section, with its height equal to the maximum table thickness and width equal to the maximum table width.

For other table configurations, the thickness is not uniform axially. The table segmentation method is found to be robust even if the table thickness is overestimated. This is because, in areas where the table is assumed to be thicker than it actually is, the scatter kernel value will be 0 since the data measurements match the air measurements. An important datum is the knowledge of h, which is the distance from the top of the table to the isocenter, thus defining the boundary of the table top and the scanned object in the projection data.

Variable Mask (Refer to Step 605)

Further refinements to the segmentation method have been developed, which include allowing the adjacent object shadow, e.g., the table shadow or mask, to be variable, rather than binary as in the above-described exemplary segmentation implementation. This may improve estimation of the adjacent object scatter profile. The variable mask method is illustrated using a patient table, but this is exemplary and not limiting.

The exemplary analytical table scatter correction algorithm as has been disclosed has two main components—the weighting function and the table mask. The weighting function is a scalar function and the table mask, corresponding to the detector area shaded by the table, is a binary 2-D map having values 1 and 0 for the regions R1 and R2, respectively. The two combine to act as a pre-weighting step in the hybrid kernel model:

$$S(x,y) = (M_{edge}(x,y) \cdot w \cdot M_{table}(x,y) \cdot A(I_p(x,y), I_0(x,y)))$$
$$\otimes h_{sym} + (M_{edge}(x,y) \cdot (1 - w \cdot M_{table}(x,y)) \cdot A(I_p(x,y), I_0(x,y)))$$
$$\otimes h_{asym}, \quad (12)$$

where $M_{edge}$ is the edge response mask, A is the amplitude part of the scatter kernel (a function of both the primary and the $I_0$ signal, as described in incorporated patent application Ser. No. 12/125,053, w is the weighting function and $M_{table}$ is the table mask resulting from table segmentation.

In the refinement, instead of a binary map, the table mask may be made variable. This means that each pencil beam passing through the table is allowed to have a different ratio of the symmetric to asymmetric kernel component. The hypothesis behind this approach is that a pencil beam that goes through the table closer to the detector may produce more symmetric scatter than a pencil beam that intersects the table further away from the detector, since it travels less distance in which scattered rays from the table may be attenuated.

The actual dependence of the table map on the table-to-detector distance is expected to be a complex function that would require extensive research to determine. Herein discloses an exemplary estimate based on first principles. The assumption is first made that the table mask intensity value should be inversely proportional the table-to-detector distance. The dependence is then adjusted based upon the scatter error remaining after correction.

To generate the exemplary distance-dependent table mask, the table-to-detector distance is computed for all pencil beams. For rays cutting through the table, the thickness of the table along the ray can be significant compared to the table-to-detector distance. Thus, the table-to-detector distance has ambiguities among the pencil beams. Because most table scatter comes from the table outer region, in this approximation the table-to-detector distance is calculated using the exit point for the table, although more complicated models could also be used.

Referring back to FIG. 8, after calculating the coordinates of the four table corners $p'_i$ and their projected locations $x_{pi}$ (i=1 . . . 4) on the detector, the table-to-detector distances are readily calculable. Note that in some cases, the projected corner may extend beyond the boundary of the physical detector. This corner would not be irradiated and it is used only as a reference point. To include all reference points, a virtual detector may be created which is big enough to include all corners of the table for all projections. The virtual detector used in this exemplary implementation is 200 cm wide and centered so it spans a range from −1000 mm to +1000 mm, with pixel index running from 1 to 2000 (pitch of 1 mm).

Figure 9:
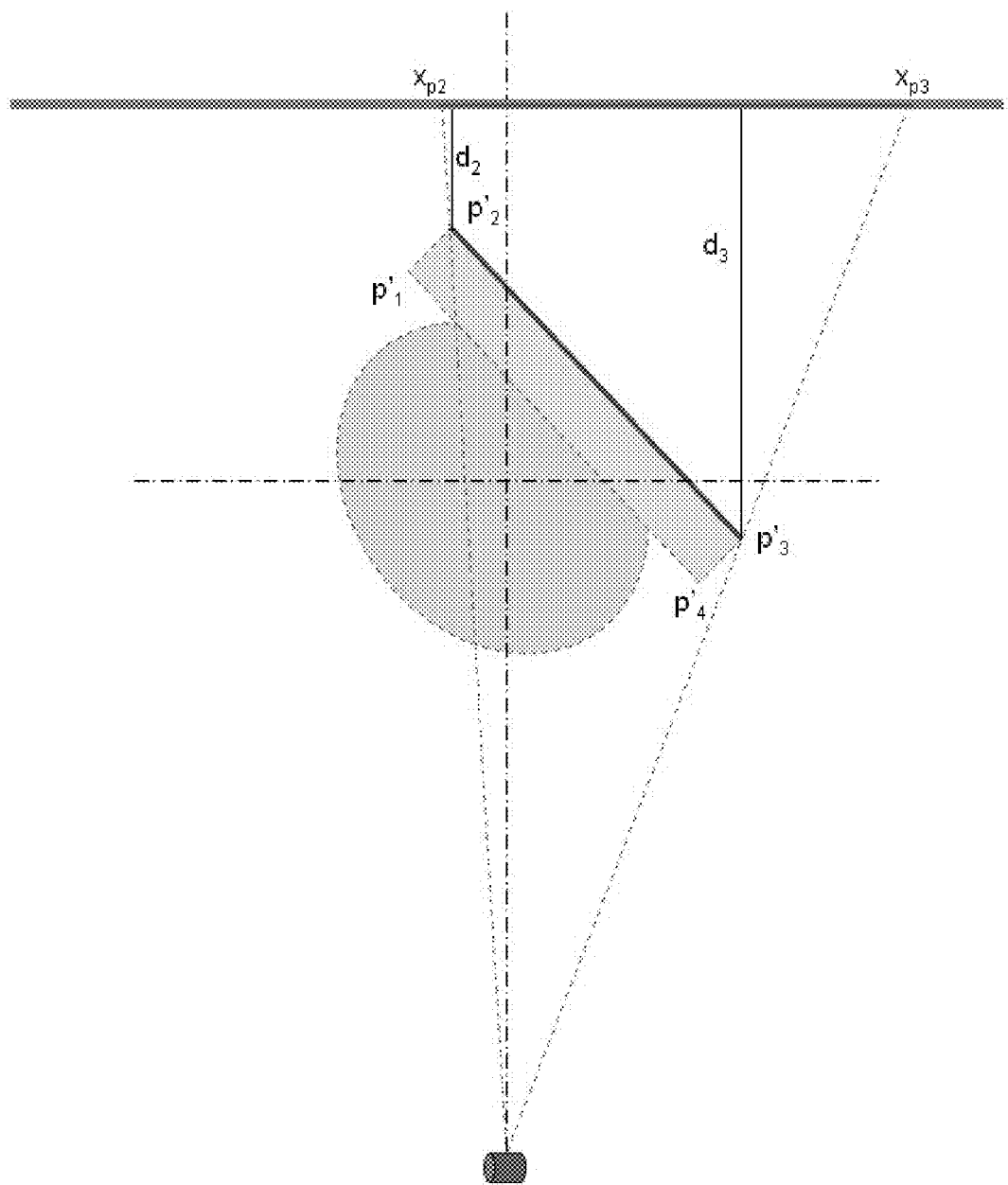
FIG. 9 illustrates the generation of a distance-weighted table mask.

FIG. 9 illustrates an exemplary generation of a distance-weighted table mask. Shown is the transaxial view of the table 900 with one of its surfaces 905 projected onto the virtual detector 910. The distance from table surface 905 to detector 910 is approximated as a linearly varying function having boundary values of $d_2$ and $d_3$ at endpoints $x_{p2}$ and $x_{p3}$. For a given projection, the two exit corners ($p'_2$ and $p'_3$) project to points $x_{p2}$ and $x_{p3}$ on the virtual detector with corresponding distances of $d_2$ and $d_3$ to the table. Note that the distances $d_2$ and $d_3$ are defined as the shortest geometrical distance from the table exit point to the detector. Then, for any ray falling between $p'_2$ and $p'_3$, a distance estimate can be linearly interpolated. The linear interpolation method is only an approximation, since for a divergent beam the distance between two straight lines varies nonlinearly. Nevertheless, this approximation is expected to be sufficiently accurate for a first estimate. The linearly interpolated distance is computed as follows:

$$r_{ab}(x) = d_a + (d_b - d_a)\frac{x - x_{pa}}{x_{pb} - x_{pa}},\qquad(13)$$

where the subscripts a and b refer to two corner rays (in this case 2 and 3).

Figure 10:
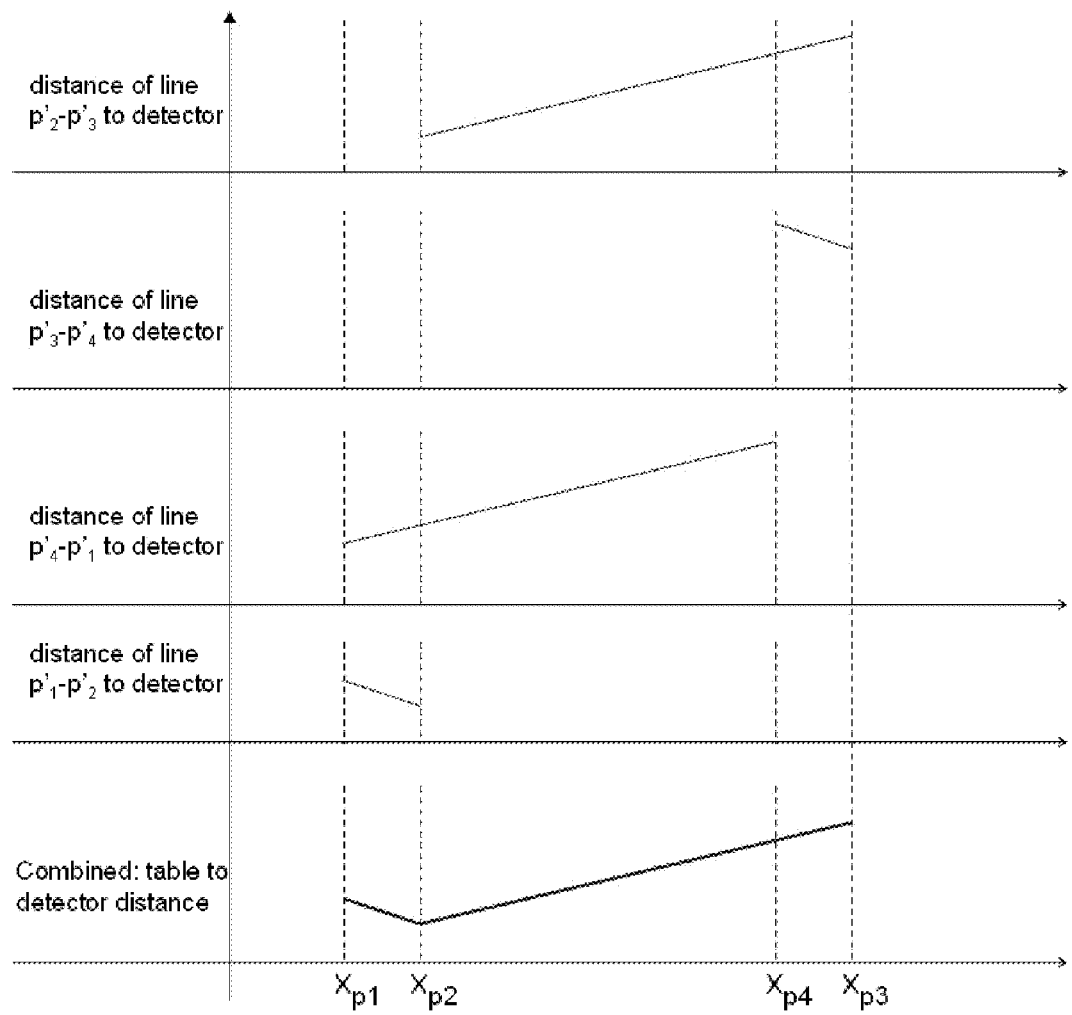
FIG. 10 illustrates the process of computing a distance from the table to the detector plane.

FIG. 10 illustrates an exemplary process of computing a distance from the table to the detector plane. The distance to the detector using a pair of table corners as a reference is first calculated, and all permutations of table corners are used. (The final table-to-detector distance is defined as the shortest distance to the detector.) After this occurs, the virtual detector is clipped to the actual detector size and resampled to determine the final distance value for each super pixel.

Once a distance map r(x,y) is obtained, the table mask may be built using the formula $$M_{table}(x, y) = k\left(\frac{DAD}{r(x, y)}\right)^q,\qquad(14)$$

where DAD is the detector-to-axis distance, and k, q are user-determined tuning parameters. It is found that k=1 and q=1 give reasonable results.

Figure 11:
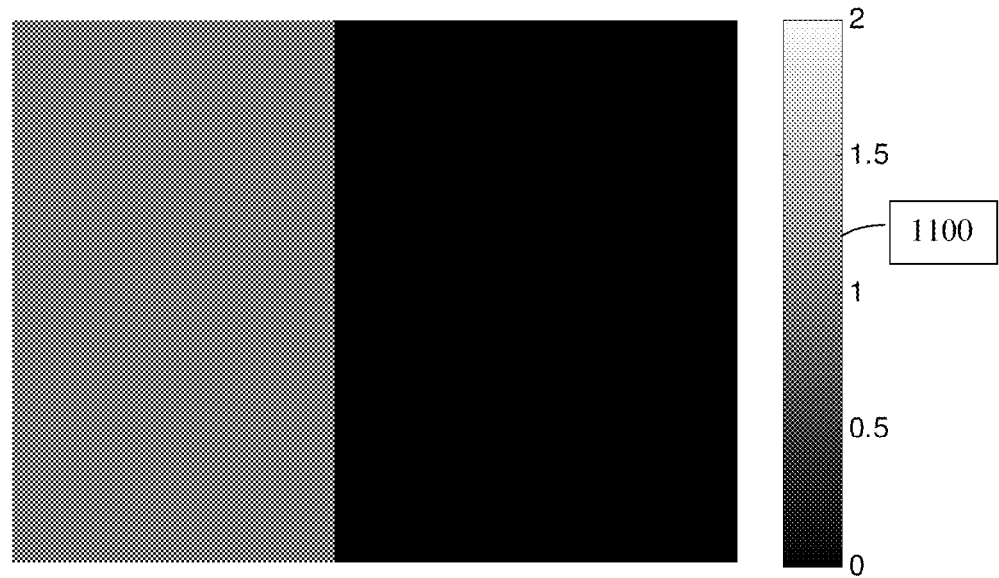
FIG. 11 shows an example of masks from binary and variable segmentation algorithms, for the same projection.
Figure 11:
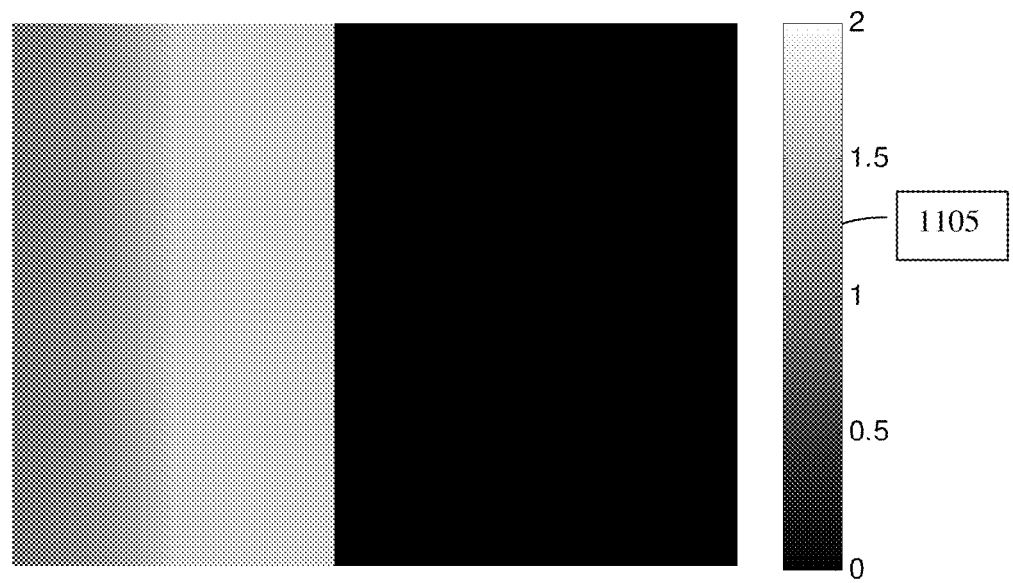

FIG. 11 shows an example of masks from binary (1100) and variable (1105) segmentation algorithms, for the same projection.

Results

Figure 12:
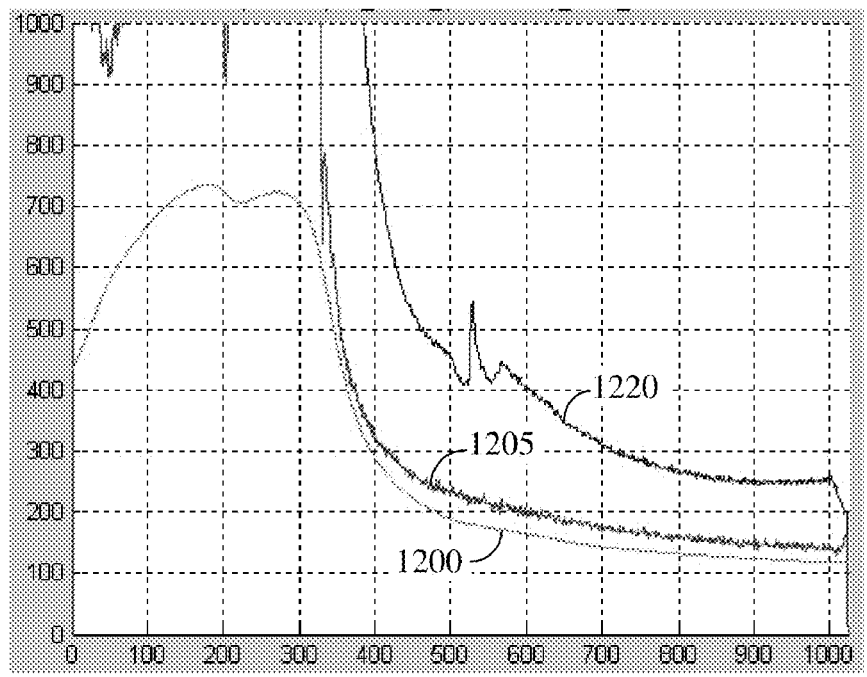
FIG. 12 shows an exemplary graph of estimated scatter and measured scatter signal vs. detector column, without and with analytical hybrid kernel method correction for patient table scatter.
Figure 12:
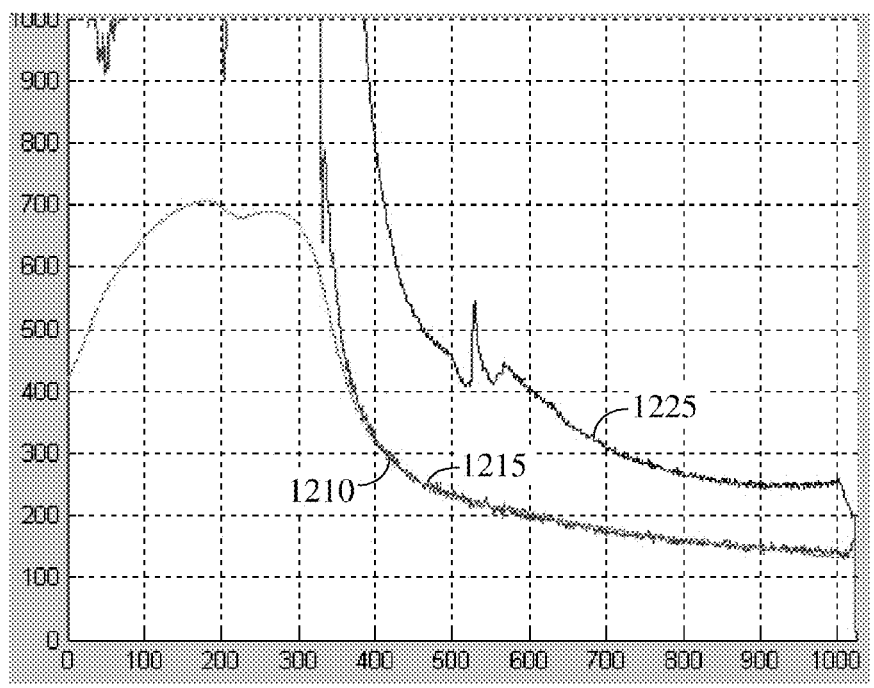

FIG. 12 shows an exemplary graph of estimated scatter and measured scatter signal vs. detector column, with (1200, 1205) and without (1210, 1215) analytical hybrid kernel method correction for patient table scatter. Upper curves 1220, 1225 are total signal, i.e., primary+scatter. It is seen that, with the patient table correction, the estimated scatter curve is quite close to the measured curve.

Figure 13:
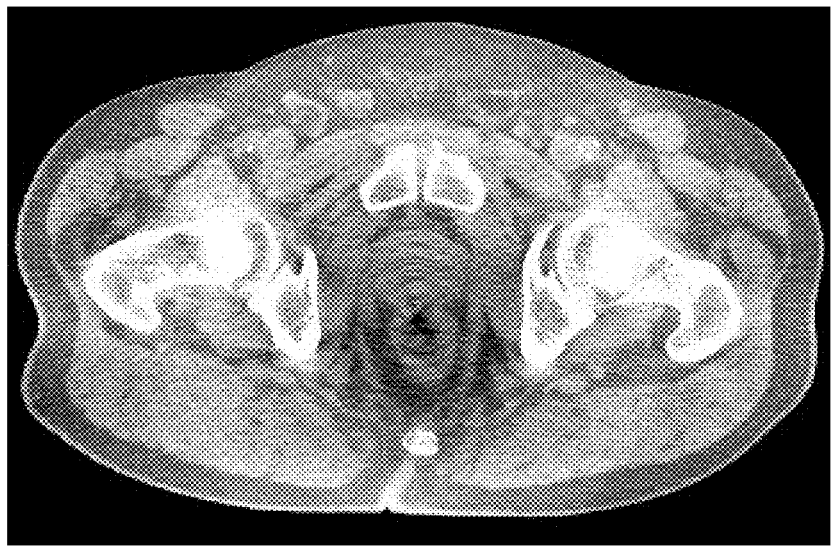
FIG. 13 shows corrected pelvis CT slices corresponding to the uncorrected slice of FIG. 3.
Figure 13:
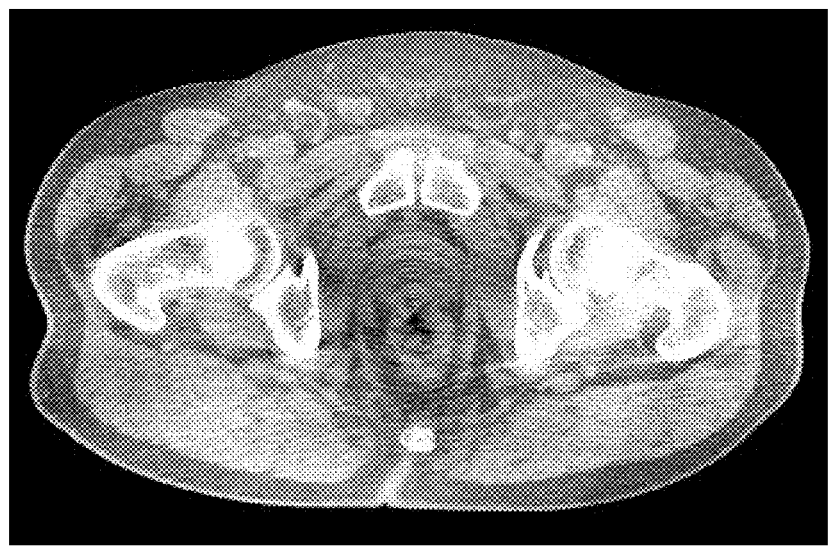

FIG. 13 shows corrected pelvis CT slices corresponding to the uncorrected slice of FIG. 3. Slice 1300 is corrected using piercing point equalization, slice 1305 is corrected using the analytical hybrid kernel model with a binary table mask. In this example, the analytical correction gives an overall flatter image, measured as 40 HU (Hounsfield Units) in the area below the isocenter.

System and Computer Program Product Embodiments

Figure 1A:
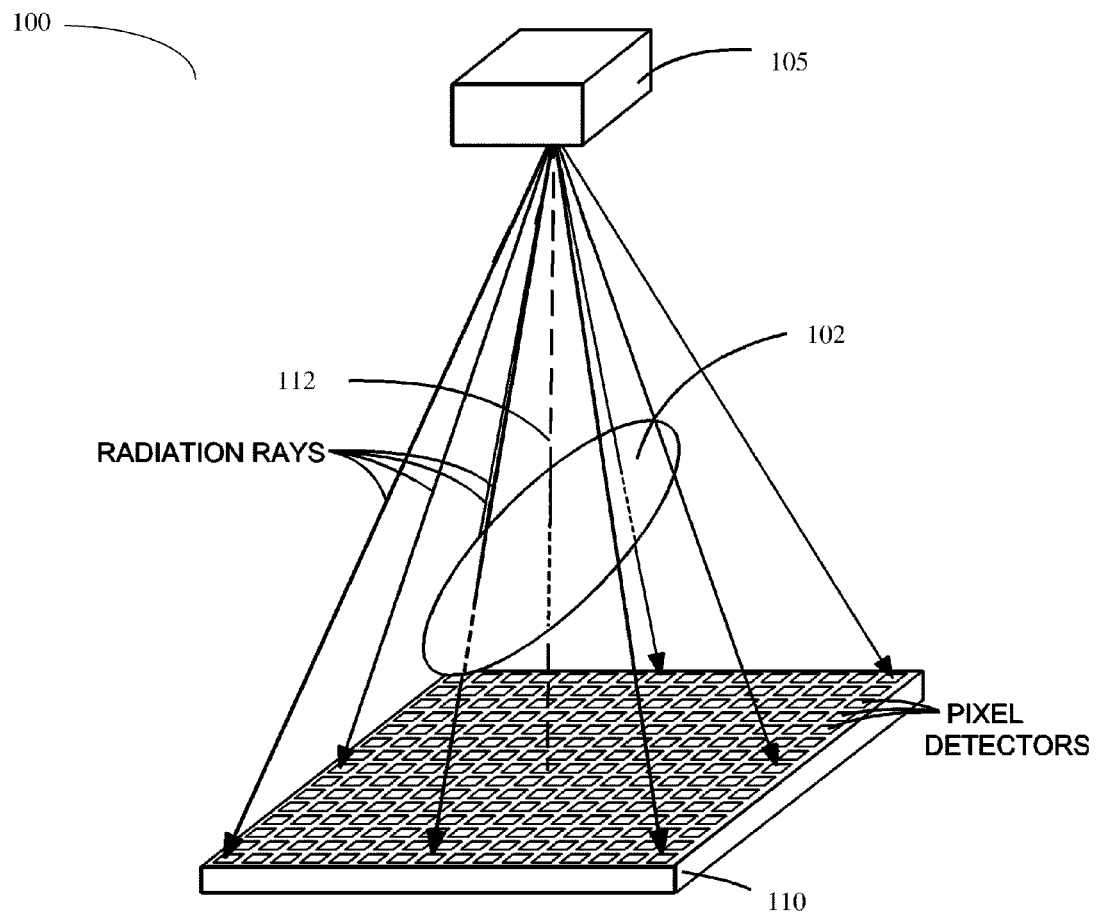
FIG. 1a is a schematic diagram of a radiation imaging system according to the prior art.
Figure 1B:
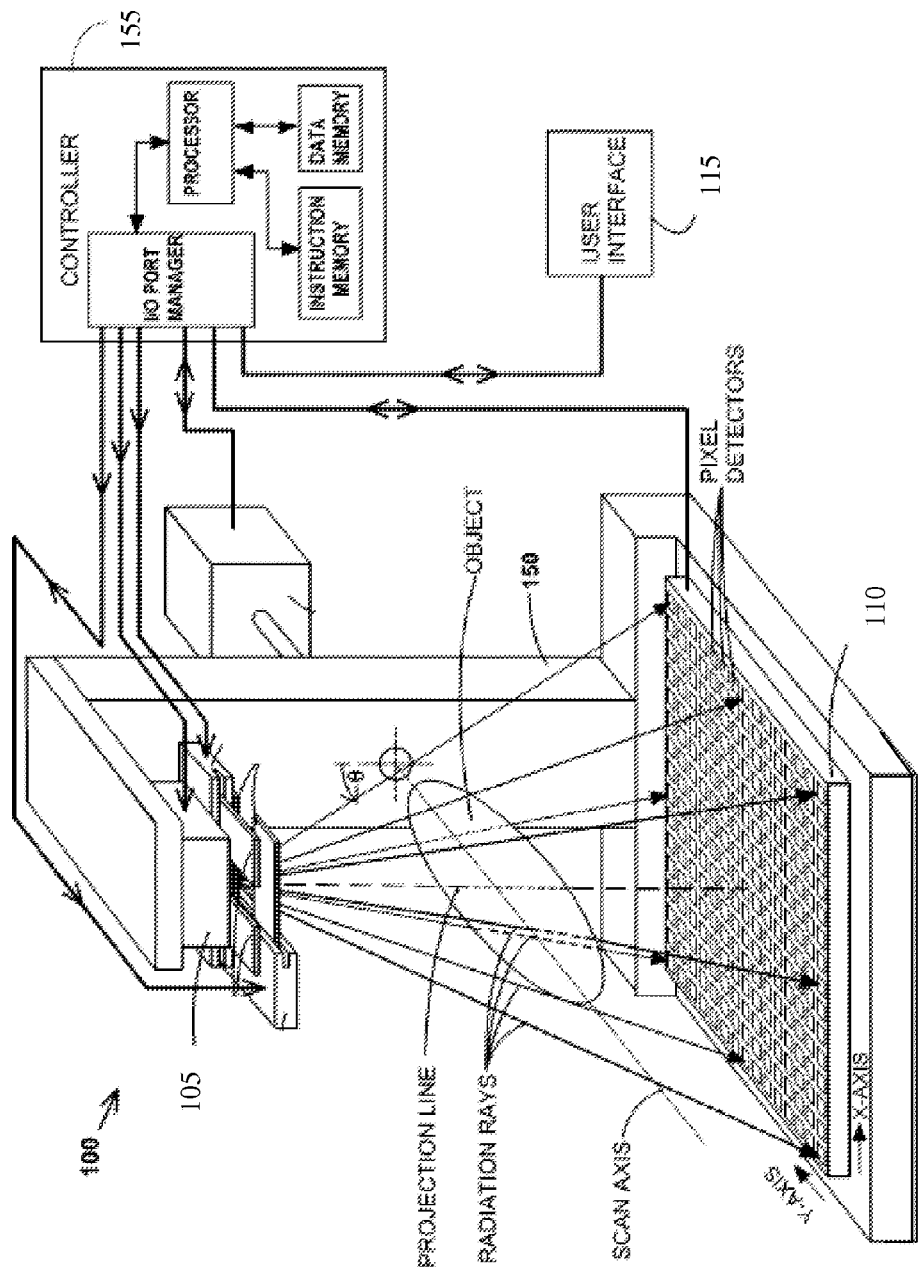
FIG. 1b is a schematic diagram of an exemplary radiation imaging system embodiment which could be used to implement some of the inventions disclosed herein. Included is a gantry and a controller.

Each of the above-described methods may be implemented by computer program products that direct a computer system to perform the actions of the methods. Each such computer program product may comprise sets of instructions embodied on a tangible computer-readable medium that direct the processor of a computer system to perform the corresponding actions. Examples of such computer-readable mediums are the instruction memory shown for controller 155 in FIG. 1b. The instructions may be in executable computer code (such as C, C++), human-readable code (such as MatLab Code), and the like. Other types of tangible computer-readable media include floppy disks, removable hard disks, optical storage media such as CD-ROMS, DVDs and bar codes, semiconductor memories such as flash memories, read-only-memories (ROMS), battery-backed volatile memories, networked storage devices, and the like. Given the above-detailed description of the various method embodiments of the inventions of the present application, it is within the skill of one of ordinary skill in the tomography art to implement each of the method embodiments disclosed herein in a computer program product without undue experimentation. Such computer program product may be run on processor 155 shown in FIG. 1b, or on separate processors that are not coupled to Cone-beam Computer Tomography Systems.

Exemplary systems of the present application may comprise radiation source 105, imaging device 110, and controller 155, in combination with various computer program products and/or methods of the present application.

Any recitation of "a", "an", and "the" is intended to mean one or more unless specifically indicated to the contrary.

The terms and expressions which have been employed herein are used as terms of description and not of limitation, and there is no intention in the use of such terms and expressions of excluding equivalents of the features shown and described, it being recognized that various modifications are possible within the scope of the invention claimed.

Moreover, one or more features of one or more embodiments may be combined with one or more features of other embodiments without departing from the scope of the invention.

While the present invention has been particularly described with respect to the illustrated embodiments, it will be appreciated that various alterations, modifications, adaptations, and equivalent arrangements may be made based on the present disclosure, and are intended to be within the scope of the invention and the appended claims.

The invention claimed is:

1. A method of forming a total estimate of scattered radiation in a radiographic projection of a target object, said scattered radiation detected by a detector, said method comprising:
    a) generating at least one radiographic projection of said target object;
    b) forming a first scatter correction estimate of said radiographic projection, said first scatter correction estimate not including scatter from an adjacent object that is at least partially adjacent to said target object;
    c) separately forming a second scatter correction estimate of said radiographic projection, said second scatter correction estimate including scatter from said adjacent object; and
    d) generating said total estimate of scattered radiation by summing said first scatter correction estimate and said second scatter correction estimate.

2. The method of claim 1, wherein b) comprises
    dividing said at least one radiographic projection into a first and a second portion, wherein exactly one of said first and said second portion, said second portion, includes a radiation projection of an adjacent object that is at least partially adjacent to said target object; and
    forming said first scatter correction estimate of said first portion.

3. The method of claim 2, wherein said first scatter correction estimate of said first portion is formed using an analytical model including generating a scatter estimation kernel for said target object.

4. The method of claim 3, wherein said scatter estimation kernel for said target object is an asymmetric kernel.

5. The method of claim 2, wherein said second scatter correction estimate of said second portion is formed using an analytical model.

6. The method of claim 5, wherein said analytical model includes generating a scatter estimation kernel for said adjacent object.

7. The method of claim 6, wherein said scatter estimation kernel for said adjacent object comprises a hybrid combination of at least a first scatter estimation kernel and at least a second scatter estimation kernel.

8. The method of claim 7, wherein said first scatter estimation kernel is a symmetric kernel and said second scatter estimation kernel is an asymmetric kernel, and wherein said hybrid combination includes a weighting factor w corresponding to a relative weighting of said symmetric kernel and said asymmetric kernel.

9. The method of claim 8, wherein said weighting factor w is a function of projection angle $\theta$, that is, a weighting function $w(\theta)$.

10. The method of claim 9, comprising for each projection:
    a) generating said $w(\theta)$;
    b) projecting said adjacent object onto said detector;
    c) dividing said detector into a first region R1 shadowed by said adjacent object, and a second region R2 not shadowed by said adjacent object;
    d) forming a first scatter estimation using asymmetric (conv1) kernels for region R2; and
    e) forming a second scatter estimation using symmetric (conv0) and asymmetric (conv1) kernels for region R1, of the form scatter=w*conv0+(1−w)*conv1; and
    f) forming a total scatter estimation equal to the sum of said first scatter estimation and said second scatter estimation; and
    g) storing said total scatter estimation on a computer-readable medium.

11. The method of claim 10, wherein said regions R1 and R2 form an adjacent object mask, said adjacent object mask being a binary 2D map having values 1 and 0 for regions R1 and R2 respectively.

12. The method of claim 10, wherein said regions R1 and R2 form an adjacent object mask, said adjacent object mask having a variable value between 0 and 1 for a given location on said detector, said variable value having a dependence on the distance between said given location on said detector and the exit point from said adjacent object of a pencil radiation beam impinging on said given location on said detector.

13. The method of claim 12, wherein said dependence is inversely proportional.

14. The method of claim 9, wherein said weighting function is approximated as a function containing weighting function parameters, said weighting function parameters being derived from an experimental determination for a particular adjacent object geometry.

15. The method of claim 14, wherein said experimental determination is provided by slit scan measurements.

16. The method of claim 9, wherein said weighting function is approximated as one of: a symmetric Gaussian function, and an asymmetric Gamma distribution function.

17. The method of claim 1, wherein c) comprises separately forming said second scatter correction estimate of said second portion.

18. The method of claim 1, wherein said adjacent object differs from said target object in at least one of: density, and material composition.

19. The method of claim 1, wherein said adjacent object is a support structure for said target object.

20. The method of claim 19, wherein said adjacent object is a patient table top.

21. The method of claim 20, wherein said patient table top comprises a carbon fiber skin layer.

22. The method of claim 1, wherein said radiographic projection is formed from a radiation source onto a detector, said radiographic projection having a projection axis, said detector being offset from said projection axis.

23. A non-transitory computer-readable medium configured to store instruction sets which, when executed by a processor of a computer system, cause the processor to estimate scattered radiation in a radiographic projection of a target object, the computer readable medium comprising: one or more instruction sets that directs the processor to perform the actions of
    a) generating at least one radiographic projection of said target object;
    b) forming a first scatter correction estimate of said radiographic projection, said first scatter correction estimate not including scatter from an adjacent object that is at least partially adjacent to said target object;

c) separately forming a second scatter correction estimate of said radiographic projection, said second scatter correction estimate including scatter from said adjacent object; and d) generating said total estimate of scattered radiation by summing said first scatter correction estimate and said second scatter correction estimate.

24. The computer-readable medium of claim 23, wherein b) comprises dividing said at least one radiographic projection into a first and a second portion, wherein exactly one of said first and said second portion, said second portion, includes a radiation projection of an adjacent object that is at least partially adjacent to said target object; and forming said first scatter correction estimate of said first portion;

and wherein c) comprises separately forming said second scatter correction estimate of said second portion.

25. The computer-readable medium of claim 24, wherein said second scatter correction estimate of said second portion is formed using an analytical model.

26. The computer-readable medium of claim 25, wherein said analytical model includes generating a scatter estimation kernel for said adjacent object.

27. The computer-readable medium of claim 2, wherein said scatter estimation kernel for said adjacent object is a hybrid combination of symmetric and asymmetric kernels, said hybrid combination including a weighting factor w corresponding to relative weighting of said symmetric kernels and said asymmetric kernels in said hybrid combination.

28. The computer-readable medium of claim 27, wherein said weighting factor w is a function of projection angle θ, that is, a weighting function w(θ).

29. The computer-readable medium of claim 28, comprising for each projection:

a) generating said w(θ);
b) projecting said adjacent object onto said detector;
c) dividing said detector into a first region R1 shadowed by said adjacent object, and a second region R2 not shadowed by said adjacent object;
d) forming a first scatter estimation using asymmetric (conv1) kernels for region R2; and
e) forming a second scatter estimation using symmetric (conv0) and asymmetric (conv1) kernels for region R1, of the form scatter=w*conv0+(1−w)*conv1; and
f) forming a total scatter estimation equal to the sum of said first scatter estimation and said second scatter estimation; and
g) storing said total scatter estimation on a computer-readable medium.

30. The computer-readable medium of claim 29, wherein said regions R1 and R2 form an adjacent object mask, said adjacent object mask being a binary 2D map having values 1 and 0 for regions R1 and R2 respectively.

31. The computer-readable medium of claim 29, wherein said regions R1 and R2 form an adjacent object mask, said adjacent object mask having a variable value between 0 and 1 for a given location on said detector, said variable value having a dependence on the distance between said given location on said detector and the exit point from said adjacent object of a pencil radiation beam impinging on said given location on said detector.

32. The computer-readable medium of claim 31, wherein said dependence is inversely proportional.

33. The computer-readable medium of claim 28, wherein said weighting function is approximated as a function containing weighting function parameters, said weighting function parameters being derived from an experimental determination for a particular adjacent object geometry.

34. The computer-readable medium of claim 33, wherein said experimental determination is provided by slit scan measurements.

35. The computer-readable medium of claim 33, wherein said weighting function is approximated as one of: a symmetric Gaussian function, and an asymmetric Gamma distribution function.

36. The computer-readable medium of claim 24, wherein said first scatter correction estimate of said first portion is formed using an analytical model including generating a scatter estimation kernel for said target object.

37. The computer-readable medium of claim 36, wherein said scatter estimation kernel for said target object is an asymmetric kernel.

38. The computer-readable medium of claim 23, wherein said adjacent object differs from said target object in at least one of: density, and material composition.

39. The computer-readable medium of claim 23, wherein said adjacent object is a support structure for said target object.

40. The computer-readable medium of claim 39, wherein said adjacent object is a patient table top.

41. The computer-readable medium of claim 40, wherein said patient table top comprises a carbon fiber skin layer.

42. The computer-readable medium of claim 23, wherein said radiographic projection is formed from a radiation source onto a detector, said radiographic projection having a projection axis, said detector being offset from said projection axis.

43. A system comprising:
a processor, said processor including the computer-readable medium according to claim 23.

44. A system comprising:
a processor, said processor including the computer-readable medium according to claim 24.

45. A system comprising:
a processor, said processor including the computer-readable medium according to claim 32.

46. A system comprising:
a processor, said processor including the computer-readable medium according to claim 29.

* * * * *